(12) United States Patent
Bi et al.

(10) Patent No.: US 9,682,982 B2
(45) Date of Patent: Jun. 20, 2017

(54) INHIBITORS OF ADAPTER ASSOCIATED KINASE 1, COMPOSITIONS COMPRISING THEM, AND METHODS OF THEIR USE

(71) Applicant: Lexicon Pharmaceuticals, Inc., The Woodlands, TX (US)

(72) Inventors: Yingzhi Bi, Plainsboro, NJ (US); Godwin Kumi, Rocky Hill, CT (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 14/658,653

(22) Filed: Mar. 16, 2015

(65) Prior Publication Data

US 2016/0039824 A1 Feb. 11, 2016

Related U.S. Application Data

(60) Provisional application No. 61/953,976, filed on Mar. 17, 2014.

(51) Int. Cl.
*C07D 487/04* (2006.01)

(52) U.S. Cl.
CPC ................. *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 8,946,415 B2* | 2/2015 | Bi .................. | A61K 31/519 544/281 |
| 8,969,565 B2* | 3/2015 | Bi .................. | C07D 487/04 546/121 |
| 2015/0164899 A1* | 6/2015 | Lanthorn ........ | A61K 31/436 514/210.18 |
| 2015/0183792 A1 | 7/2015 | Bi | |

OTHER PUBLICATIONS

International Search Report for International Application No. PCT/US2015/020696 filed Mar. 16, 2015.

* cited by examiner

*Primary Examiner* — Alexander R Pagano
*Assistant Examiner* — Ebenezer O Sackey
(74) *Attorney, Agent, or Firm* — Max Bachrach

(57) ABSTRACT

The adaptor associated kinase 1 (AAK1) inhibitor 3-methyloxetan-3-yl-4-(3-(2-methoxypyridin-3-yl)pyrazolo[1,5-a]pyrimidin-5-yl)piperazine-1-carboxylate:

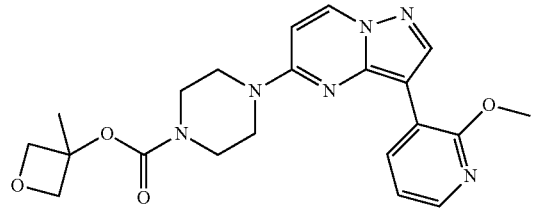

Figure 1:
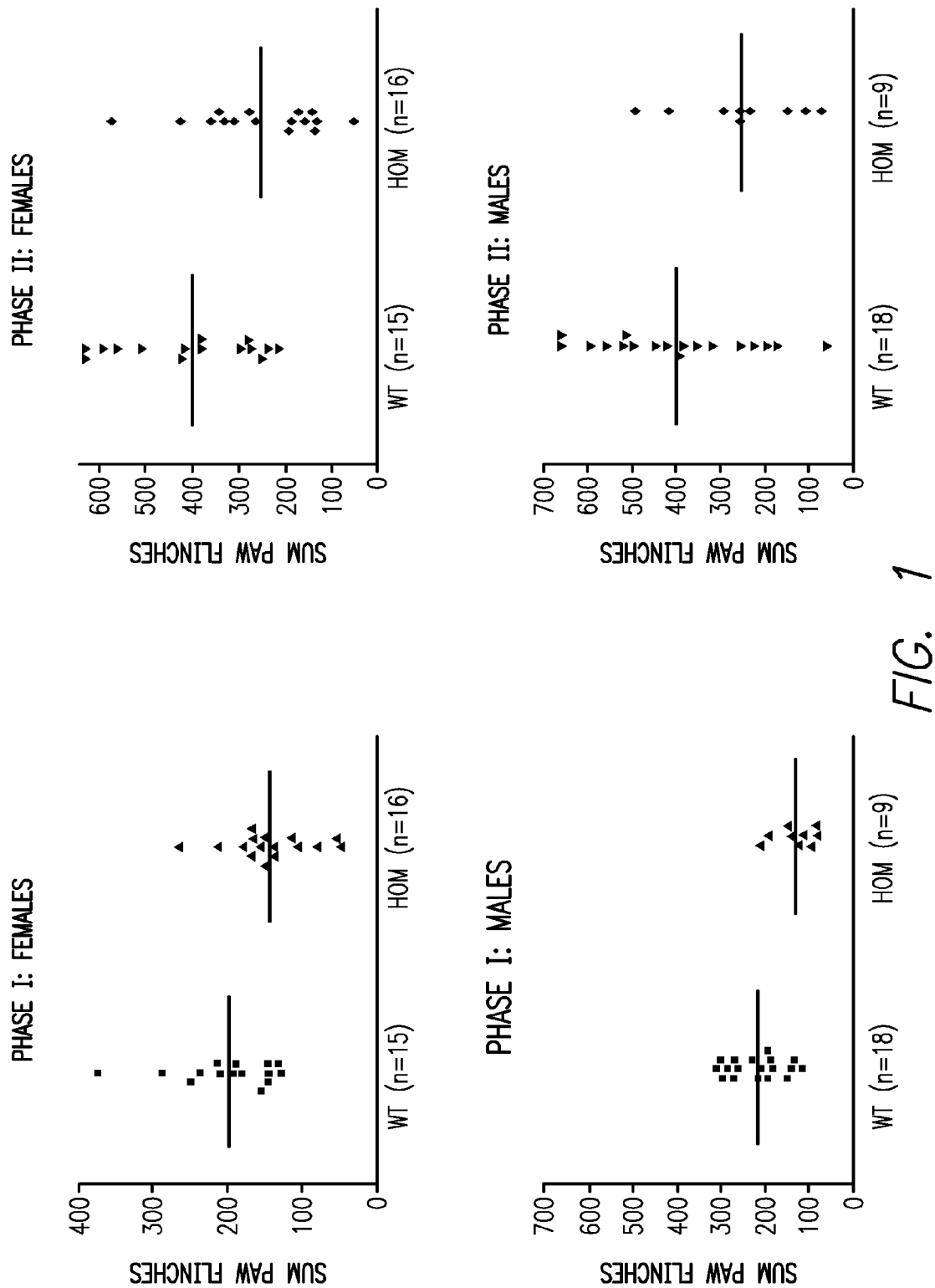

and pharmaceutically acceptable salts and solid forms thereof are disclosed. Compositions comprising the compound and methods of their use to treat, manage and/or prevent diseases and disorders mediated by mediated by AAK1 activity are also disclosed.

10 Claims, 6 Drawing Sheets

INHIBITORS OF ADAPTER ASSOCIATED KINASE 1, COMPOSITIONS COMPRISING THEM, AND METHODS OF THEIR USE

This application claims priority to U.S. provisional patent application No. 61/953,976, filed Mar. 17, 2014, the entirety of which is incorporated herein by reference.

1. FIELD OF THE INVENTION

This invention is directed to pyrazolo[1,5-a]pyrimidine-based compounds useful as inhibitors of adaptor associated kinase 1 (AAK1), compositions comprising them, and methods of their use.

2. BACKGROUND OF THE INVENTION

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., *Proc. Natl. Acad. Sci. USA.* 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, bipolar disorder, and Alzheimer's disease.

3. SUMMARY OF THE INVENTION

This invention encompasses 3-methyloxetan-3-yl-4-(3-(2-methoxypyridin-3-yl)pyrazolo[1,5-a]pyrimidin-5-yl)piperazine-1-carboxylate:

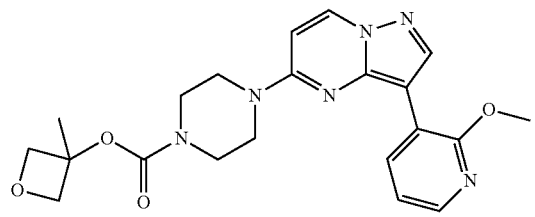 [SMILES: COc1ncccc1-c1cnn2ccc(N3CCN(C(=O)OC4(C)COC4)CC3)nc12]

and pharmaceutically acceptable salts and solid forms (e.g., crystalline forms) thereof. Pharmaceutical compositions and dosage forms comprising the compound are also encompassed by the invention.

One embodiment of this invention encompasses methods of inhibiting adaptor associated kinase 1 (AAK1), both in vitro and in vivo, which comprise contacting AAK1 with a compound of the invention.

Another embodiment encompasses methods of treating and managing diseases and disorders mediated by AAK1 activity. Examples of such diseases and disorders are believed to include Alzheimer's disease, bipolar disorder, pain, Parkinson's disease, and schizophrenia (including cognitive deficits in schizophrenia).

4. BRIEF DESCRIPTION OF THE FIGURES

Some aspects of the invention are illustrated in the figures.

FIG. 1 shows results obtained from a formalin pain model using AAK1 homozygous (−/−) knockout mice and their wild-type (+/+) littermates. The AAK1 homozygous (−/−) knockout mice show a clear reduction in both acute and tonic pain response as compared to their wild-type (+/+) littermates.

Figure 2:
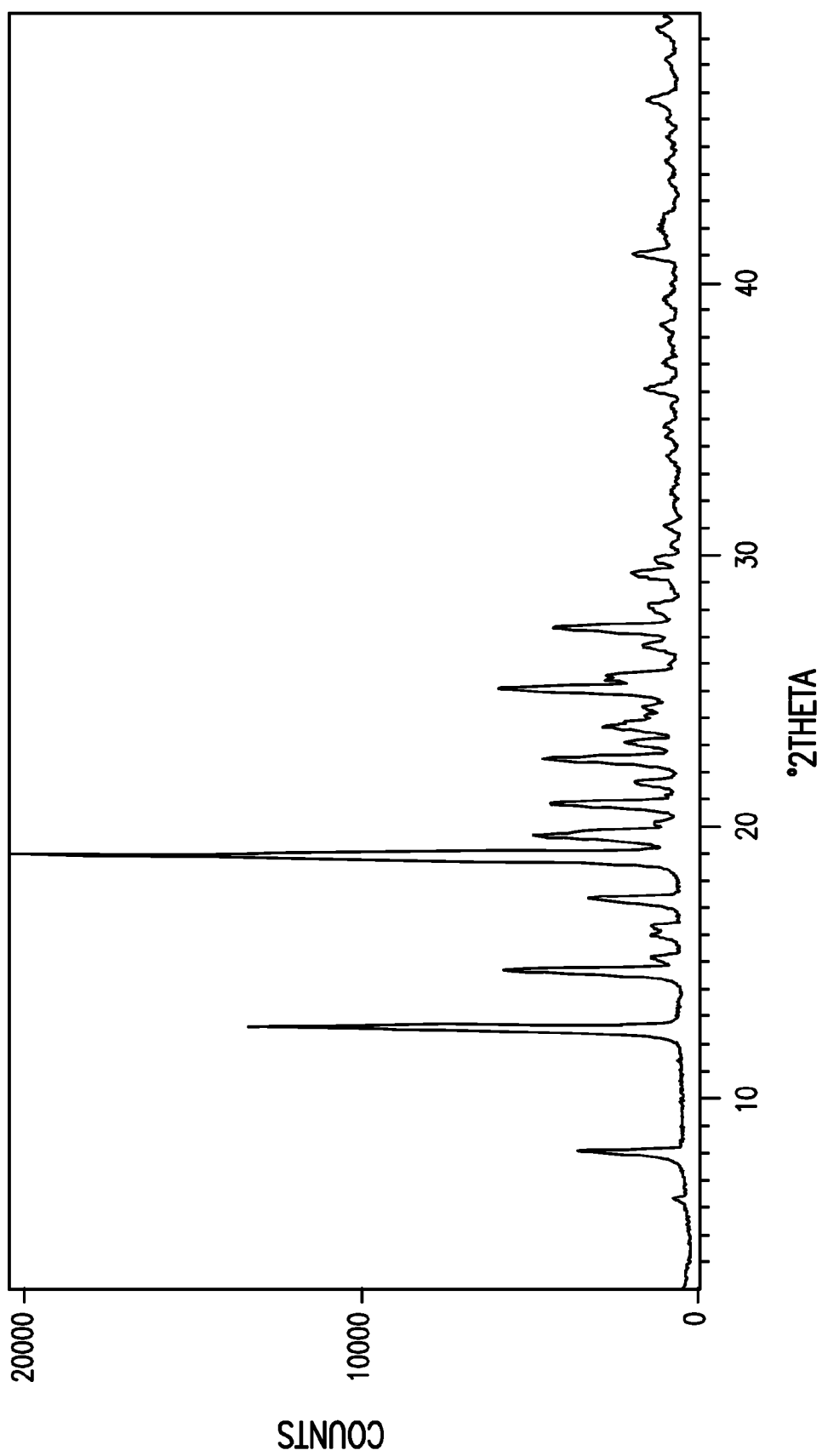

FIG. 2 provides an X-ray diffraction spectrum of crystalline 3-methyloxetan-3-yl-4-(3-(2-methoxypyridin-3-yl)pyrazolo[1,5-a]pyrimidin-5-yl)piperazine-1-carboxylate. The diffractogram was obtained using a PANalytical X'Pert PRO (Cu Kα radiation) with a PIXcel Medipix2 detector (40 mA, 45 kV; 0.0260° 2θ step size).

Figure 3:
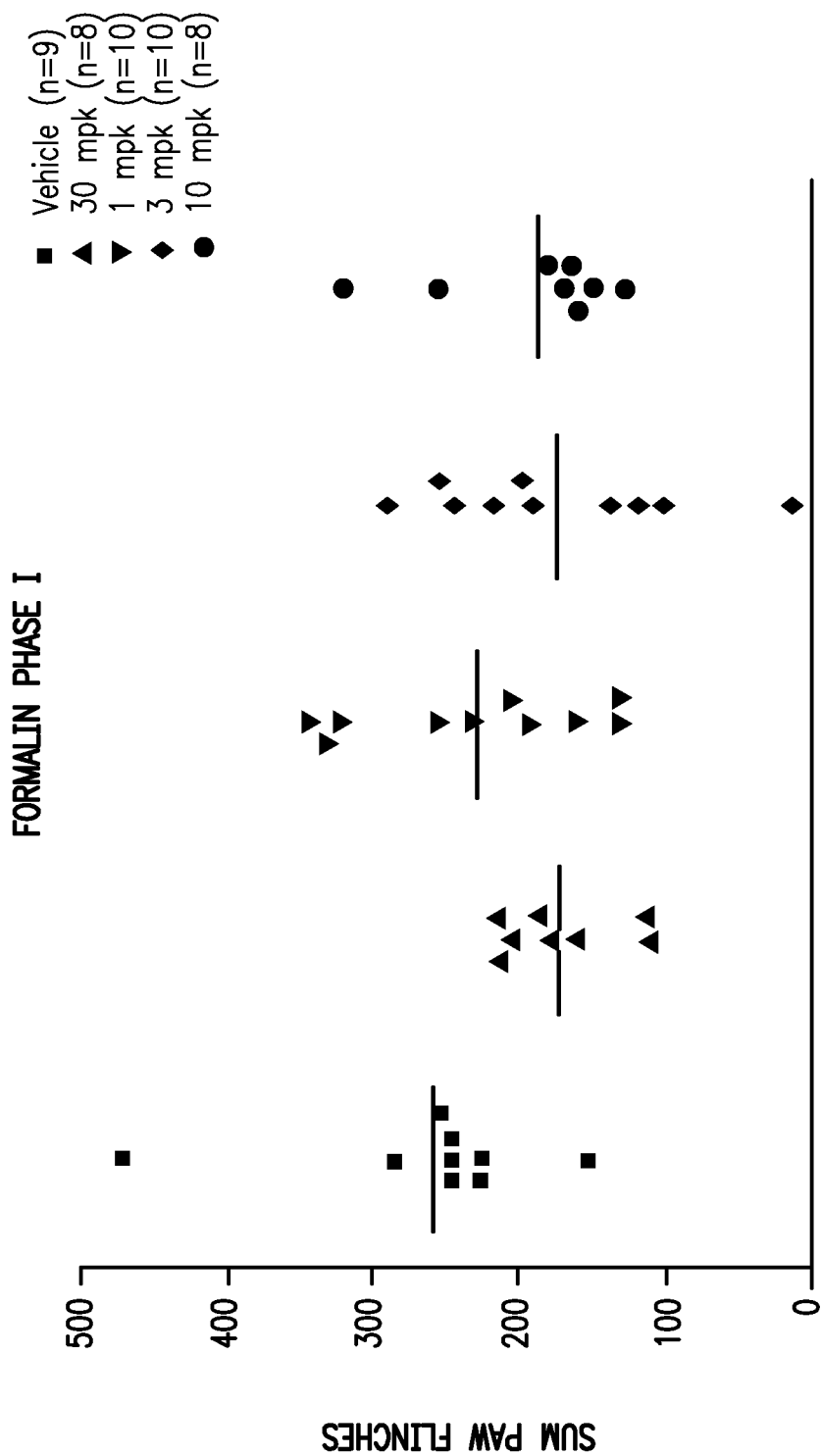

FIG. 3 shows formalin phase 1 data obtained for 3-methyloxetan-3-yl-4-(3-(2-methoxypyridin-3-yl)pyrazolo[1,5-a]pyrimidin-5-yl)piperazine-1-carboxylate in male C57 mice, with doses of 1, 3, 10 and 30 mpk compared to vehicle.

Figure 4:
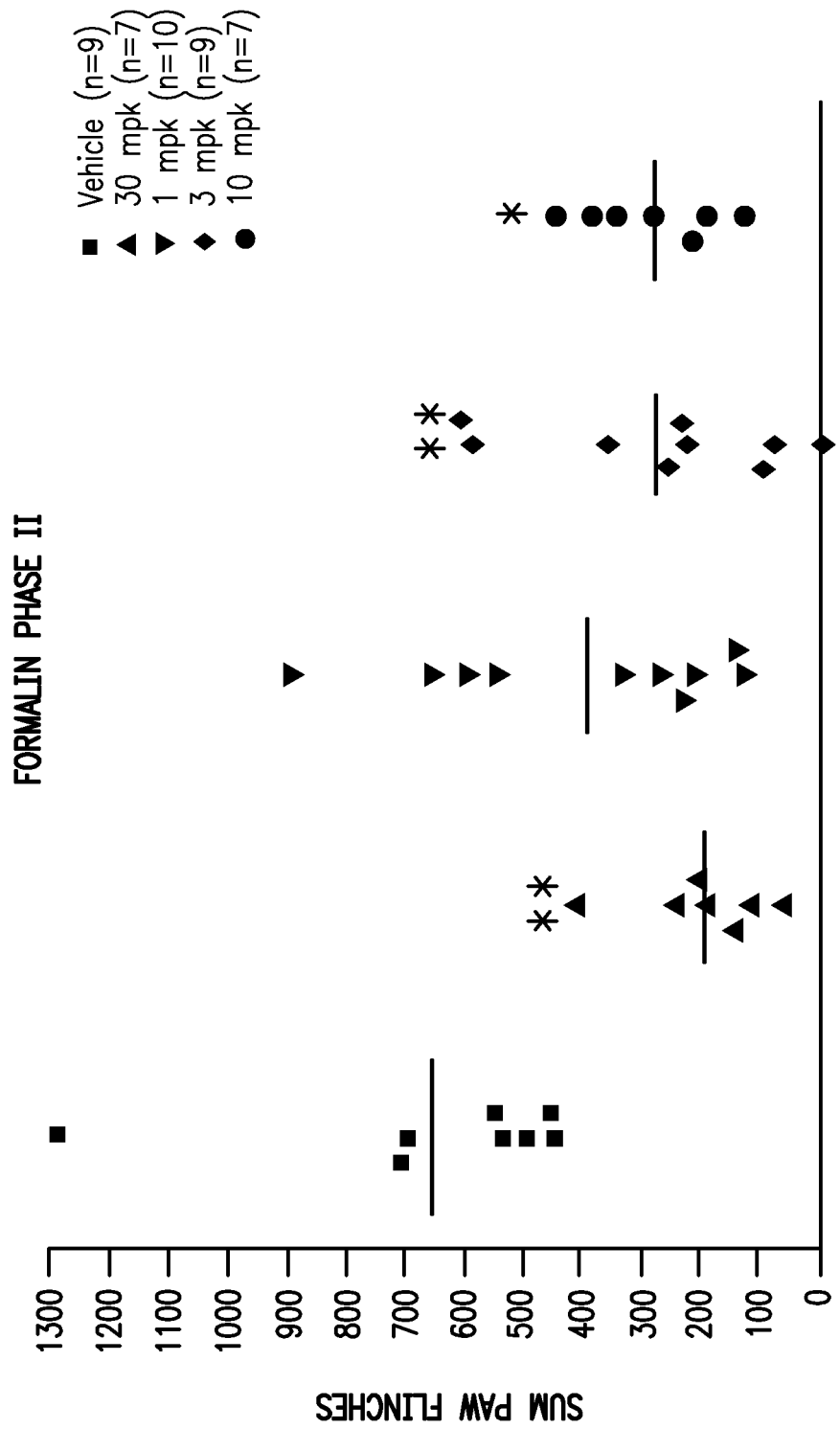

FIG. 4 shows formalin phase 2 data obtained for the compound in male C57 mice, with doses of 1, 3, 10 and 30 mpk compared to vehicle.

Figure 5:
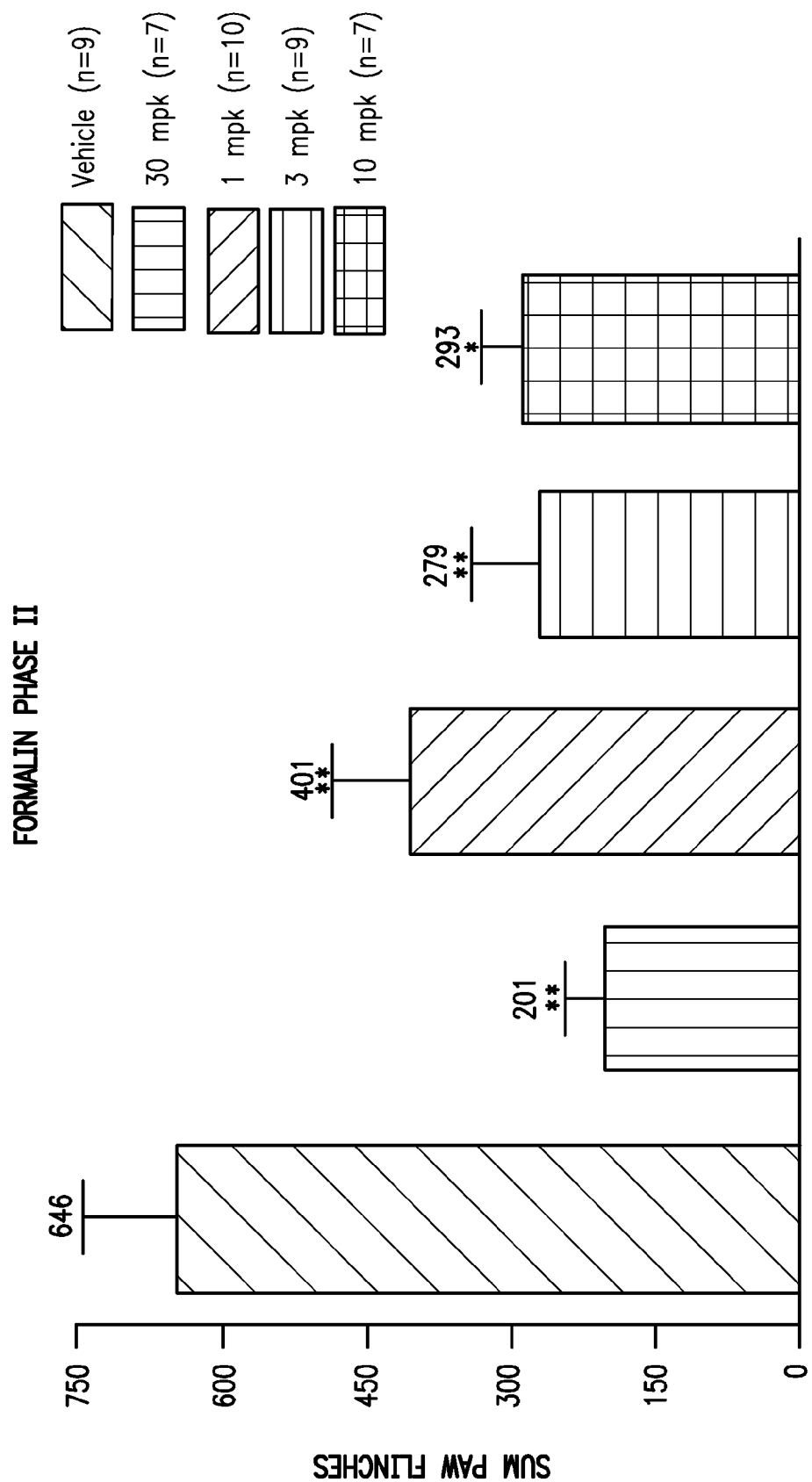

FIG. 5 provides a bar graph representation of the data shown in FIG. 4.

Figure 6:
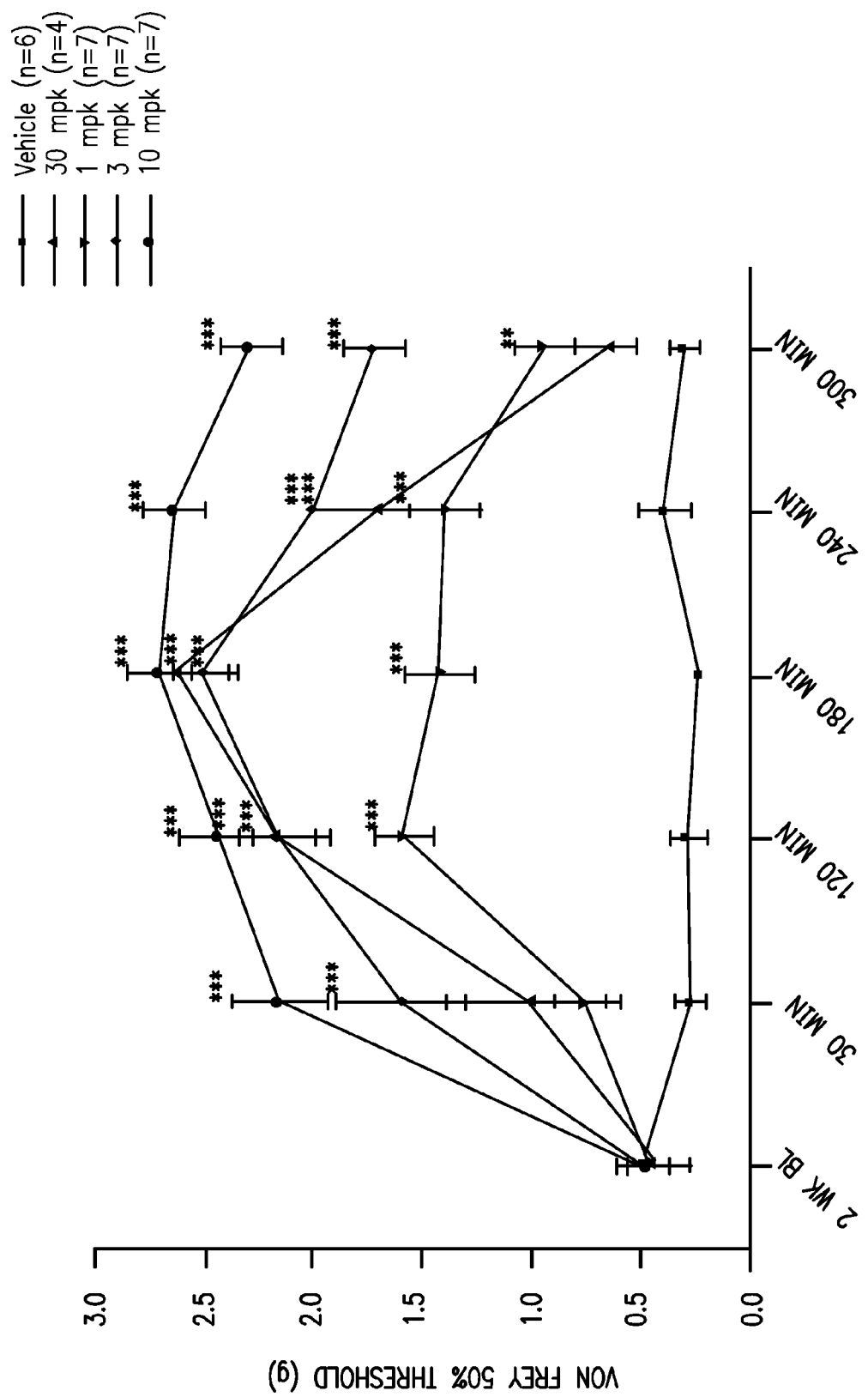

FIG. 6 shows the dose-dependent effect of the compound in the mouse Chung assay.

5. DETAILED DESCRIPTION OF THE INVENTION

This invention is based, in part, on the discovery that AAK1 knockout mice exhibit a high resistance to pain. That discovery prompted research that ultimately led to the discovery of AAK1 inhibitors, compositions comprising them, and methods of their use.

5.1. DEFINITIONS

Unless otherwise indicated, the phrases "compounds of the invention," "compounds of the present disclosure," and the like refer to the compounds disclosed herein.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

5.2. COMPOUNDS

This invention encompasses 3-methyloxetan-3-yl-4-(3-(2-methoxypyridin-3-yl)pyrazolo[1,5-a]pyrimidin-5-yl)piperazine-1-carboxylate:

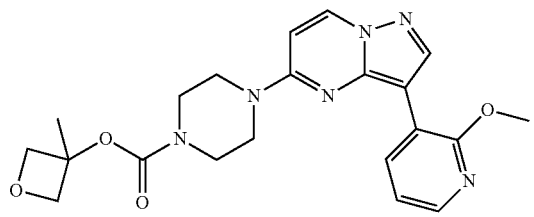 [SMILES: COc1ncccc1-c1cnn2ccc(N3CCN(C(=O)OC4(C)COC4)CC3)nc12]

and pharmaceutically acceptable salts thereof.

This invention further encompasses crystalline forms of 3-methyloxetan-3-yl-4-(3-(2-methoxypyridin-3-yl)pyrazolo [1,5-a]pyrimidin-5-yl)piperazine-1-carboxylate. In one embodiment, a crystalline form has a melting point of about 182.5° C. as determined by differential scanning calorimetry. In this context, the term "about" means±2.0 degrees centigrade.

In one embodiment, a crystalline form of the compound provides an X-ray powder diffraction (XRPD) pattern that contains peaks at one or more of about 12.7, 14.8, 18.7, 19.0, 19.7 and/or 25.1 degrees 2θ when obtained using Cu Kα radiation. In this context, the term "about" means±0.2 degrees 2θ. As those skilled in the art are well aware, the relative intensities of peaks in an XRPD pattern can vary depending on how the sample is prepared and how the data is collected. With this in mind, an example of an XRPD pattern of this form is provided in FIG. 2.

Compounds of the invention may exist in different stable conformational forms, which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

This invention encompasses isotopomers, or isotopic isomers, of the compounds disclosed herein, wherein the isotopes of one or more atoms within a compound are different from those which naturally or generally occur. By way of general example and without limitation, isotopes of hydrogen include deuterium and tritium. Isotopes of carbon include $^{13}C$ and $^{14}C$. Isotopically-labeled compounds of the invention can be prepared by conventional techniques known to those skilled in the art (e.g., by using an appropriate isotopically-labeled reagent in place of the non-labeled reagent otherwise employed). Such compounds may have a variety of potential uses, for example as standards and reagents in determining biological activity. In the case of stable isotopes, such compounds may have the potential to favorably modify biological, pharmacological, or pharmacokinetic properties.

Compounds of this invention may exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, diydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

5.3. METHODS OF USE

One embodiment of this invention encompasses methods of inhibiting adaptor associated kinase 1 (AAK1), both in vitro and in vivo, which comprise contacting AAK1 with a compound of the invention.

Another embodiment encompasses methods of treating and managing diseases and disorders mediated by AAK1 activity. Diseases and disorders mediated by AAK1 activity are diseases and disorders that have at least one symptom, the severity or manifestation of which is affected by AAK1 activity. Examples of such diseases and disorders are believed to include Alzheimer's disease, bipolar disorder, pain, Parkinson's disease, and schizophrenia (including cognitive deficits in schizophrenia). Particular methods comprise administering to a patient (a human or other mammal) in need thereof a therapeutically or prophylactically effective amount of a compound of the invention.

Another embodiment of this invention encompasses a method of treating or managing a disease or disorder, which comprises administering to a patient in need thereof a therapeutically or prophylactically effective amount of a compound of the invention, wherein the disease or disorder is Alzheimer's disease, bipolar disorder, pain, Parkinson's disease, or schizophrenia (including cognitive deficits in schizophrenia). Particular types of pain include chronic pain, acute pain, and neuropathic pain. Particular types of neuropathic pain include fibromyalgia and peripheral neuropathy (e.g., diabetic neuropathy).

When used to treat or manage a disease or disorder, compounds of the invention are preferably administered as part of a pharmaceutical composition comprising one or more pharmaceutically acceptable carriers, diluents or excipients.

Pharmaceutical compositions, or formulations, may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

Compounds of the invention may be administered in combination with one or more additional therapeutic or prophylactic agents. For example, when used for the treatment of pain, possible additional agents include immunosuppressive and anti-inflammatory agents.

Immunosuppressants suitable for use in the methods and compositions of this invention include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Additional examples include inosine monophosphate dehydrogenase inhibitors, such as mycophenolate mofetil (CellCept®) and mycophenolic acid (Myfortic®).

Anti-inflammatory drugs suitable for use in the methods and compositions of this invention include those known in the art. Examples include glucocorticoids and NSAIDs.

Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the invention may be administered in combination with one or more additional therapeutic or prophylactic agents directed at the underlying disease or condition. For example, when used to treat diabetic neuropathy, compounds of the invention may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

5.4. PHARMACEUTICAL COMPOSITIONS

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

Compounds of the invention may be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

Compounds of the invention may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

5.5. EXAMPLES

5.5.1. AAK1 Knockout Mice

Mice homozygous (−/−) for the disruption of the AAK1 gene were prepared by two methods: gene trapping and homologous recombination.

Gene trapping is a method of random insertional mutagenesis that uses a fragment of DNA coding for a reporter or selectable marker gene as a mutagen. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Embryonic stem cells (Lex-1 cells from derived murine strain A129), were mutated by a process involving the insertion of at least a portion of a genetically engineered vector sequence into the gene of interest, the mutated embryonic stem cells were microinjected into blastocysts which were subsequently introduced into pseudopregnant female hosts and carried to term using established methods. See, e.g., "Mouse Mutagenesis", 1998, Zambrowicz et al., eds., Lexicon Press, The Woodlands, Tex. The resulting chimeric animals were subsequently bred to produce offspring capable of germline transmission of an allele containing the engineered mutation in the gene of interest.

AAK1-gene disrupted mice were also made by homologous recombination. In this case, the second coding exon of the murine AAK1 gene (see GenBank Accession Number NM_177762) was removed by methods known in the art. See, e.g., U.S. Pat. Nos. 5,487,992, 5,627,059, and 5,789, 215.

Mice homozygous (−/−) for the disruption of the AAK1 gene were studied in conjunction with mice heterozygous (+/−) for the disruption of the AAK1 gene, and wild-type (+/+) litter mates. During this analysis, the mice were subject to a medical work-up using an integrated suite of medical diagnostic procedures designed to assess the function of the major organ systems in a mammalian subject. Homozygous (−/−) "knockout" mice were studied in conjunction with their heterozygous (+/−) and wild-type (+/+) litter mates. Disruption of the AAK1 gene was confirmed by Southern analysis. Expression of the murine homolog of AAK1 was detected by RT-PCR in murine brain; spinal cord; eye; thymus; spleen; lung; kidney; liver; skeletal muscle; bone; stomach, small intestine and colon; heart; adipose; asthmatic lung; LPS liver; blood; banded heart; aortic tree; prostate; and mammary gland (5 week virgin, mature virgin, 12 DPC, 3 day post-partum (lactating), 3 day post-weaning (early involution), and 7 day post-weaning (late involution)).

AAK1 homozygous (−/−) and their wild-type (+/+) littermates were tested using the formalin paw test described below in Example 5.5.6 in order to assess their acute and tonic nociceptive responses.

As shown in FIG. 1, phase 1 and phase 2 data were obtained using homozygous (−/−) mice females (n=16), wild-type females (n=15), homozygous (−/−) mice males (n=9), and wild-type males (n=18). In all groups and in both phases, the AAK1 homozygous (−/−) mice exhibited significantly less recorded paw flinching than their wild-type (+/+) littermates.

5.5.2. Synthesis of 3-Methyloxetan-3-yl-4-(3-(2-methoxypyridin-3-yl)pyrazolo[1,5-a]pyrimidin-5-yl)piperazine-1-carboxylate

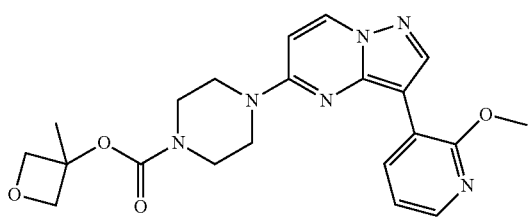 [SMILES: COc1ncccc1-c1cnn2ccc(N3CCN(C(=O)OC4(C)COC4)CC3)nc12]

Part A. 3-bromo-5-chloropyrazolo[1,5-a]pyrimidine

To a mixture 5-chloropyrazolo[1,5-a]pyrimidine (30 g, 195 mmol) in acetonitrile (600 mL) was added N-bromosuccinimide (38.3 g, 215 mmol). The mixture was stirred at room temperature for 1 hour. Solid product was filtered off and washed with 1N NaOH and water. Acetonitrile filtrate and all the washes was concentrated in vacuo and suspended in 1N NaOH. The solid product was filtered and washed with water. This product was combined with previous solid and dried overnight to obtain 44.2 g 3-bromo-5-chloropyrazolo [1,5-a]pyrimidine. LRMS (ESI) m/z 232/234 [(M+H)]+, calc'd for $C_6H_3BrClN_3$: 232.47. LCMS (M+1, bromo pattern)=233. $^1$H NMR (400 MHz, $CDCl_3$) δ: 6.82 (d, 1H), 8.15 (broad S, 1H), 8.58 (d, 1H).

Part B. 3-bromo-5-(piperazin-1-yl)pyrazolo[1,5-a]pyrimidine

To an solution of 3-bromo-5-chloropyrazolo(1,5-a)pyrimidine (25 g, 0.107 mol) in 1,4-dioxane (500 ml) was added triethylamine (43 g, 0.43 mol), followed by piperazine (28 g, 0.322 mol). The reaction mixture was stirred at 90° C. for 4 h. After completion of reaction, it was diluted with ethyl acetate and washed with water. The water layer was back extracted with ethyl acetate. The combined organic layer was dried over sodium sulfate and evaporated to obtain 35 g of crude 3-bromo-5-(piperazine-1-yl)pyrazolo(1,5-a) pyrimidine. The product could be recrystallized from methanol but generally used without further purification. $^1$H NMR (400 MHz, DMSO-$d_6$) δ 2.74-2.81 (m, 4H), 3.55-3.69 (m, 4H), 6.75 (d, J=7.83 Hz, 1H), 7.94 (s, 1H), 8.62 (d, J=7.83 Hz, 1H). $^{13}$C NMR (100 MHz, DMSO-$d_6$) δ ppm 41.25, 42.16, 77.73, 97.78, 136.77, 144.01, 144.18, 155.53. LRMS (ESI) m/z 282.0/284.0 [(M+H)]+, calc'd for $C_{10}H_{12}BrN_5$: 282.14.

Part C. 3-(2-methoxypyridin-3-yl)-5-(piperazin-1-yl)pyrazolo[1,5-a]pyrimidine

The 3-bromo-5-(piperazin-1-yl)pyrazolo[1,5-a]pyrimidine (3.00 g, 10.64 mmol), (2-methoxypyridin-3-yl)boronic acid (2.44 g, 15.96 mmol) and bis(di-tert-butyl(4-dimethylaminophenyl)phosphine)dichloropalladium(II) (0.23 g, 0.32 mmol) were weighed into a 200 mL round bottom flask. Then 60 mL of dioxane was added, followed by the addition of 30 mL of water and then triethylamine (7.40 mL, 53.19 mmol). The resulting mixture was heated to 85° C., after 1.5 hr the reaction was completed. Then it was concentrated to dryness on the rotavap. The solid residue was suspended in water and the pH adjusted to about 2 using HCl. Three extractions were done with EtOAc to remove the impurities. The pH was then adjusted to about 8 using NaOH. The suspension was cold in an ice bath for about 1 hr to enhance precipitation of the desired product. The solid was filtered and dried to obtain 2.74 g (83%) of the titled compound as a pale yellow solid. $^1$H NMR (400 MHz, METHANOL-$d_4$) δ ppm 2.92-3.07 (m, 4H), 3.72-3.84 (m, 4H), 4.08 (s, 3H), 6.73 (d, J=8.03 Hz, 1H), 7.04 (dd, J=7.53, 5.02 Hz, 1H), 7.95 (dd, J=4.89, 1.88 Hz, 1H), 8.46 (d, J=8.03 Hz, 1H), 8.53 (s, 1H), 8.89 (dd, J=7.53, 1.76 Hz, 1H). LRMS (ESI) m/z 311.1 [(M+H)]+, calc'd for $C_{16}H_{18}N_6O$: 310.4.

Part D. 3-methyloxetan-3-yl (4-nitrophenyl) carbonate

The 3-oxetanone (7.00 g, 97.22 mol) dissolved in 200 mL of THF in a 500 mL round bottom flask was cooled to −20° C. whilst stirring over nitrogen. Then, 34.0 mL (105.08 mmol) of methyl magnesium bromide (3M ether solution) was slowly added over a period of 15 minutes. (The reaction becomes thick, and a little difficult to stir.) The cooling bath was removed, and the reaction allowed stir and warm to rt. After 2.5 hr, the reaction was cooled to 0° C., and quenched by slowing adding 100 mL of saturated aq. $NH_4Cl$ and afterwards a few drops of 1N HCl added to adjust the pH to about 6. Extract twice with 200 mL portions of DCM. The combined organic layer was dried over $MgSO_4$. It was filtered and concentrated on the rotavap with no heat. An oil, 6.19 g was obtained containing 81% of the desired product and 19% of THF was obtained based on proton NMR analysis. Estimated yield of the reaction was (5.14 grams) 60%. $^1$H NMR (400 MHz, CHLOROFORM-d) δ 1.58 (s, 3H), 4.49 (d, J=7.28 Hz, 2H), 4.63 (d, J=6.53 Hz, 2H).

To 4.32 g of 3-methyl-oxetan-3-ol (81% w/w in THF, 39.77 mmol) dissolved in 40 mL DCM was cooled to 0° C. The pyridine was added, followed by the addition of the 4-nitrophenyl chloroformate in small portions over a period of 10 minutes. The solution became cloudy and the ice-bath was removed, and stirring was allowed to continue for under nitrogen at room temperature. After 1 hr, a clear pale yellow solution was obtained. The reaction was quenched with water and extracted twice with DCM. The combined organic layer was washed with brine and dried over $MgSO_4$, and concentrated. It was loaded onto a 330 column using a small volume of DCM and subjected to separation on the ISCO using only DCM as solvent to obtain 6.2 g (61%) of the desired product. $^1$H NMR (400 MHz, CHLOROFORM-d) δ 1.86 (s, 3H), 4.57 (d, J=8.03 Hz, 2H), 4.90 (d, J=7.53 Hz, 2H), 7.41 (d, J=6.51 Hz, 2H), 8.31 (d, J=6.42 Hz, 2H).

Part E. 3-methyloxetan-3-yl 4-(3-(2-methoxypyridin-3-yl)pyrazolo[1,5-a]pyrimidin-5-yl)piperazine-1-carboxylate To a mixture of methoxy-pyridin-3-yl)-5-piperazin-1-yl-pyrazolo[1,5-a]pyrimidine (1 g, 3.22 mmol) and 3-methyl-oxetan-3-yl (4-nitrophenyl) carbonate (979 mg, 3.87 mmol) in acetonitrile was added DIEA (2.24 mL, 12.9 mmol). The mixture was stirred at room temp for 6 hours. The reaction mixture was diluted with 1N NaOH 50 mL and filtered. The solid was washed with 1N NaOH, water, and heptane. Product was recrystallized from dioxane:water and then recrystallized again from acetonitrile to afford 950 mg of 3-methyloxetan-3-yl 4-(3-(2-methoxypyridin-3-yl)pyrazolo [1,5-a]pyrimidin-5-yl)piperazine-1-carboxylate. $^1$H NMR (700 MHz, DMSO-$d_6$) δ 1.67 (s, 3H), 3.52 (br. s., 2H), 3.58 (br. s., 2H), 3.80 (br. s., 4H), 4.01 (s, 3H), 4.43 (d, J=7.06 Hz, 2H), 4.67 (d, J=7.06 Hz, 2H), 6.84 (d, J=7.82 Hz, 1H), 7.09 (dd, J=7.34, 4.86 Hz, 1H), 7.99 (d, J=3.43 Hz, 1H), 8.52 (s, 1H), 8.77 (d, J=7.82 Hz, 1H), 8.82 (d, J=7.91 Hz, 1H). LRMS (ESI) m/z 425 [(M+H)]+, calc'd for $C_{21}H_{24}N_6O_4$: 424.46.

5.5.3. P81 Filter Plate Assay

Compounds were serially diluted into a Labcyte LDV plate (Labcyte, cat #LP-0200) using a Mutiprobe (PerkinElmer) and Biomek FX (Beckman Coulter) so that the highest compound concentration was at 96 µM. Compounds were then pinged (75 nL per well) into a Greiner 384-well reaction plate (Greiner, #781076) using an ECHO 550 Liquid Handler (Labcyte). A total of 12 µl reaction buffer (IMAP buffer containing Tween and DTT, from Molecular Devices) was then added to each well of columns 1 and 13 for the negative controls and 12 µl of 2×AAK1 (0.2 nM full-length human protein, NCBI accession no. NP_055726.2) was added to the remaining wells. Enzyme was then pre-incubated with compound for 10 minutes at RT. Reactions were initiated upon Minitrak (PerkinElmer) addition of 12 μl substrate mix containing 2× Mu2 (0.2 μM, full length human protein), 2× cold ATP (2 μM), and 1.3 μCi of hot $^{33}$P-ATP. Reactions proceeded for one hour at RT. Meanwhile, Millipore 384-well P81 filter plates (Millipore, catalog #MZPHNOW10) were placed on a plate washer (Zoom ZW, from Titertek) and pre-wet with 50 μl 1% phosphoric acid. Kinase reactions were then stopped upon addition of 24 μl of 2% phosphoric acid to each well and the Minitrak was then used to transfer 40 μl from each well into the pre-wet Millipore 384-well P81 filter plates. Reaction mixtures were incubated for 10 minutes at RT in the P81 plates, followed by washing five times with 100 μl well of 1% phosphoric acid using the Zoom filter washer. The bottom of each filter plate was sealed followed by addition of 20 μl Microscint 40 to each well, sealing the top of the plates with Flashplate cover, and then waiting one hour until reading on the TopCount (PerkinElmer).

5.5.4. HEK281 Cell-Based Assay

HEK293F cells were cultured in media containing DMEM (Gibco, cat. #11965), 10% FBS (SAFC Biosciences, cat. #12103C), 1×GPS (glutamine, penicillin and streptomycin). On day one, cells were plated on a 10 cm dish so that they are ~80% confluent at time of transfection. Roughly 12 million cells were in a 10 cm dish at time of transfection. On day two, each dish was transfected with 48 ug DNA and 144 ul Lipofectamine 2000 (Invitrogen, cat. #11668-019). The DNA was comprised of a mixture (per 10 cm dish) containing 3 ug AAK1/HA/pIRES (full length human, NCBI accession no. NP_055726.2), 45 μg Flag/AP2MI/pcDNA (full length human), and 1.5 ml OPTI-MEM. The Lipofectamine 2000 is made up of a mixture (per 10 cm dish) containing 144 μl Lipofectamine 2000 and 1.5 ml OPTI-MEM. Each mixture was transferred to individual 15 ml tubes and incubated at RT for 5 minutes, and then the two mixes were combined and incubated at RT for 20 minutes. Growth media was then aspirated from each 10 cm plate and replaced with 10 ml of DMEM+10% FBS (no GPS). Finally, 3 ml DNA/Lipofectamine mix was added to each 10 cm dish and mix gently followed by incubate of plate overnight at 37° C. and 5% $CO_2$.

On day three, compounds were diluted in 100% DMSO at 1000× final concentration, followed by 3-fold serial dilutions for a total of 5 concentrations tested. Four compounds were tested per 10 cm dish. One ul of each compound dilution was then pipetted into a deep-well, 96-well plate, followed by addition of 500 μl DMEM+0.5% FBS into each well for a 2× final concentration of each compound. Cells were resuspended in a 10 cm dish by simple pipetting (HEK293 cells come off the plate that easy at this point) and then transferred to a 50 ml conical tube and pelleted by centrifugation at 1000 rpm for 5 min. Cell pellets were then resuspended in 2.75 ml DMEM+0.5% FBS per 10 cm dish and 100 μl of cell suspension transferred into each well of 96-well TC plate. Finally, 100 μl of 2× compound diluted in DMEM+0.5% FBS was then added into wells containing cell suspension for a 1× final concentration. Plates were then incubated at 37° C. and 5% $CO_2$ for 3 hours followed by transferring of cell suspensions from each well into 12-tube PCR strips. The PCR strips were spun in a tip rack at 1000 rpm for 5 minutes to pellet cells and media was then removed by pipetting without disturbing the cell pellet.

To prepare for Western Blot analysis, cell pellets were resuspend in 40 ul 1×LDS-PAGE sample buffer (Invitrogen, cat. #NP0008)+2× Halt phophatase and protease inhibitor cocktail (Thermo Scientific, cat. #1861284), followed by sonicating each with microtip sonicator set at 5 for 8-10 seconds. Five ul of 10× NuPage Sample Reducing Agent (with 50 mM DTT) was to each sample followed by heat denaturing at 70 C for 10 min on PCR machine. A total of 10 μl per sample was loaded into each lane of a 4-20% Tris-Glycine Criterion 26-well gel (Biorad, cat. #345-0034) for the phospho-mu2 blot and 10 μl per lane in a 4-12% Bis-Tris (+MES buffer) NuPAGE 26-well gel (Invitrogen, cat. #WG1403BX10) for the mu2 blot. For controls, 2 ng of phospho-mu2 or 20 ng mu2/Flag proteins were loaded in the last well of each gel. After SDS-PAGE, samples on each gel were transferred to PVDF membrane using an iBlot and membranes were blocked for one hour in TBST+5% milk, followed by wash 3× for 5-10 min with TBST. Criterion gels were probed with rabbit anti-phospho-mu2 (1:5000; a rabbit polyclonal antibody produced by New England Peptide and affinity purified at Lexicon) in TBST+5% BSA, whereas, NuPAGE gels were probed with mouse anti-Flag (1:500; Sigma, cat. #F1804) in TBST+5% milk, and these primary antibodies were incubated overnight at 4° C. on a rocker.

On day four, Western blots were washed 3× for 5-10 minutes with TBST, probe with anti-rabbit-HRP (1:2000; BioRad, cat. #170-6515) or anti-mouse-HRP (1:2000; Biorad, cat. #170-6516) in TBST+5% milk for 1 hour at RT, washed 3× for 10 minutes with TBST, and developed with ECL reagent (GE Healthcare, cat. #RPN2132) on a Versadoc. Finally, the camera was set up to take a picture every 30 seconds for 10 minutes and the best image saved for each blot with no saturated signal (when the signal is saturated, the bands will be highlighted red). A volume analysis on each band was performed to obtain density values. Percent inhibition was calculated for each sample by first normalizing to total Mu2 expression levels and then comparing to 0% and 100% controls. $IC_{50}$ values were then calculated using Excel fitting software.

5.5.5. In Vitro Data

In vitro data were obtained for 3-methyloxetan-3-yl-4-(3-(2-methoxypyridin-3-yl)pyrazolo[1,5-a]pyrimidin-5-yl)piperazine-1-carboxylate using the methods described above. In the P81 assay, the compound measured 0.9 nM. In the HEK281 cell-based assay, the compound measured 4.7 nM.

5.5.6. Formalin Assay

Mice were tested for nociception with Automatic Nociception Analyzers (purchased from the Ozaki lab at University of California, San Diego). A metal band was placed around the left hind paw of each mouse with superglue 30 minutes prior to testing. After the 30-minute acclimation period, 20 μl of 5% formalin was subcutaneously injected in the dorsal surface of the left hind paw. Mice were individually housed in cylindrical chambers for 45 minutes. Fresh 5% formalin solution was prepared by diluting formaldehyde (Formalde-fresh 20%, Fisher Scientific, Fair Lawn, N.J.) with distilled water. Investigatory compounds were administered 30 minutes prior to formalin injection.

A computer software recorded flinches per minute, total flinches for Phase I (acute phase=first 8 minutes), and total flinches for Phase II (tonic phase between 20-40 minutes) through an electromagnetic field. See Yaksh T L, Ozaki G, McCumber D, Rathbun M, Svensson C, Malkmus S, Yaksh M C. An automated flinch detecting system for use in the formalin nociceptive bioassay. *J Appl Physiol.*, 2001; 90:2386-402.

FIG. 3 shows phase 1 data obtained for 3-methyloxetan-3-yl-4-(3-(2-methoxypyridin-3-yl)pyrazolo[1,5-a]pyrimidin-5-yl)piperazine-1-carboxylate in male C57 mice, with doses of 1, 3, 10 and 30 mpk compared to vehicle.

FIG. 4 shows phase 2 data obtained for the compound in male C57 mice, with doses of 1, 3, 10 and 30 mpk compared to vehicle, wherein the statistics provided are one-way ANOVA P<0.01 dose effect, post-hoc Dunnett's: *P<0.05, P<0.01 versus vehicle. The dramatic effect of the compound is readily apparent in the bar graph of the data provided in FIG. 5**.

5.5.7. Mouse Chung Assay

The compound 3-methyloxetan-3-yl-4-(3-(2-methoxypyridin-3-yl)pyrazolo[1,5-a]pyrimidin-5-yl)piperazine-1-carboxylate was studied in the Chung assay. See Chaplan S R, Bach F W, Pogrel J W, Chung J M, Yaksh T L., *Quantitative assessment of tactile allodynia in the rat paw*, *J Neurosci Methods* 1994; 53:55-63; Chung J M, Kim H K, Chung K., *Segmental spinal nerve ligation model of neuropathic pain*, Methods Mol Med. 2004; 99:35-45.

Wild-type hybrid (C57BL/6J-Tyr$^{c-Brd}$×129S5/SvEvBrd) male mice were between 5-7 weeks of age at the time of spinal nerve ligation by the conventional Chung protocol. Spinal nerve ligation was carried out according to the procedure devised by Kim and Chung with modifications. Briefly, mice were anesthetized with isoflurane (2% at the oxygen flow rate of 1 ml/min). A skin incision (1 cm) was made 1 mm to the left of the dorsal midline, using the level of iliac crests as the mid point of the incision. The paraspinal muscles were bluntly separated medial to the iliac crest to reveal transverse processes between the caudal edge of L4 and the rostral edge of L6 (or sacroiliac junction in mice that had only five LV). This approach facilitated identification of spinal nerves L4, L5, and/or L6. In an initial experiment using hybrid mice, the presumptive locations of spinal nerve L5 and L6 were determined by using the sacroiliac junction as the landmark to locate L6, as previously described in SNL models in rats and mice. In compound test experiments using C57 mice, the position of the last two lumbar transverse processes in relation to the iliac crest was used to differentiate mice with five LV from those with six. Using these bone landmarks, the number of LV a mouse possess were accurately identified in majority of cases. L4 and L5 spinal nerve identification was made not only according to their relevant position to transverse processes but also by the gross observation of the nerves: L3 and L4 spinal nerves exclusively joined each other in the surgical field while L5 stayed alone. The left L4 and/or L5 spinal nerves were isolated and tightly ligated with 7-0 silk suture. To ligate L4, L4 was separated from L3, and a glass hook was used to pull the suture out under L4. Ligation of L5 was performed by passing suture under L5 with one pair of fine forceps and pulling the suture out from the other side with another pair of fine forceps. In very rare cases when L3 and L4 merged under L5 transverse process, L4 ligation can be made at the proximal level to the rostral edge of L5 transverse process. There was therefore no need to excise the transverse process. In sham-operated animals, the surgical procedure was identical to that as described above, except that spinal nerves were not ligated. In the spinal nerve transections performed on a fourth cohort of mice, L4 or L5 spinal nerves were cut across using fine microsurgical scissors at the same level where ligatures would normally be placed. After hemostasis was confirmed, the incision was closed in two layers, with 5-0 vicryl suture for the dorsolumbar fascia and wound clips for the skin. Mice were given an injection of saline (1 ml) and buprenorphine (0.05-0.1 mg/kg mice) immediately following the surgery and buprenorphine again at approximately 12 and 24 hours post-surgery (for a total of 3 doses) to relieve surgery-induced pain. A warming pad and a heating lamp were used to maintain normal body temperature in the animal throughout the surgery. Mice were individually housed after the procedure and were monitored until complete recovery from anesthesia.

Von Frey tactile allodynia was assessed by testing the hindpaw withdrawal response (withdrawal, flinching, licking) to a set of von Frey filaments (numbered 2.44, 2.83, 3.22, 3.61, 4.08, and 4.31 corresponding approximately to force of 0.04, 0.07, 0.16, 0.4, 1, and 2 gm, Stoelting Co. Wood Dale, Ill.) in an up-down procedure as described by Chaplan et al. Baseline von Frey tests were carried out prior to surgery, and repeated once a week for 3 to 6 weeks after surgery depending on experimental design. For the von Frey tests, mice were placed in transparent polyethylene terephthalate cylinders (10" height/4.25" diameter) with a ¼" wire mesh floor to allow the experimenter to apply the von Frey filament to the mouse plantar surface. Both paws were tested. The first von Frey filament applied was 3.61. If no response was elicited, the next stronger filament was presented. If there was a response the next weaker filament was presented. There were a total of six presentations of von Frey filaments (if the animal did not respond to the strongest filament, 4.31, the test was ended). The 50% withdraw threshold was calculated for each paw using the up down method. Mice that exhibited 50% withdraw threshold below 2 in any paw during baseline testing were excluded from surgery and further assessment. Von Frey test experimenters were always blind to the nature of the surgery and the treatment.

In order to reduce exploratory locomotor activity, mice were habituated to the testing chambers for 60 minutes the day before pre-surgery baseline testing and for 30 minutes in the chambers prior to von Frey test in which a compound was given. White noise was on in the testing room throughout the experiment.

As shown in FIG. 6, compound 3-methyloxetan-3-yl-4-(3-(2-methoxypyridin-3-yl)pyrazolo[1,5-a]pyrimidin-5-yl) piperazine-1-carboxylate exhibited a dose-dependent, significantly significant effect in the Chung assay. Overall, P<0.0001 in RM ANOVA; post-hoc Dunnett's: P<0.01, *P<0.001 versus vehicle.

All publications (e.g., patents and patent applications) cited above are incorporated herein by reference in their entireties.

What is claimed is:

1. A compound, which is 3-methyloxetan-3-yl-4-(3-(2-methoxypyridin-3-yl)pyrazolo[1,5-a]pyrimidin-5-yl)piperazine-1-carboxylate:

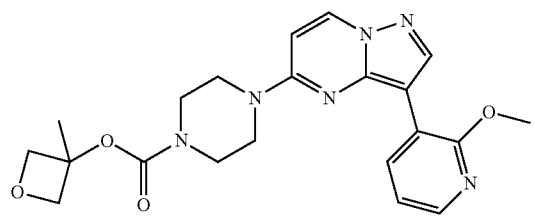 [SMILES: COc1ncccc1-c1cnn2ccc(N3CCN(C(=O)OC4(C)COC4)CC3)nc12]

or a pharmaceutically acceptable salt thereof.

2. The compound of claim 1, which is crystalline.

3. The compound of claim 2, which has a melting point of about 182.5° C.

4. The crystalline compound of claim 2, which has an X-ray powder diffraction pattern with peaks at about 12.7, 14.8, 18.7, 19.0, 19.7 and/or 25.1 degrees 2θ.

5. A method of inhibiting adaptor associated kinase 1 (AAK1) activity, comprising contacting AAK1 with a compound of claim 1.

6. A pharmaceutical composition comprising a compound of claim 1 and a pharmaceutically acceptable excipient or diluent.

7. A method of treating or managing a disease or disorder mediated by AAK1 activity, which comprises administering to a patient in need thereof a therapeutically effective amount of a compound of claim 1, or a pharmaceutical composition of claim 6.

8. The method of claim 7, wherein the disease or disorder is Alzheimer's disease, bipolar disorder, pain, Parkinson's disease, or schizophrenia.

9. The method of claim 8, wherein the pain is neuropathic pain.

10. The method of claim 9, wherein the neuropathic pain is fibromyalgia or peripheral neuropathy.

* * * * *